United States Patent [19]
Venuto et al.

[11] Patent Number: 5,620,409
[45] Date of Patent: Apr. 15, 1997

[54] METHOD FOR INHIBITING CLOT FORMATION

[75] Inventors: Rocco C. Venuto, Williamsville, N.Y.; Reinold O. B. Gans, Maarsen, Netherlands

[73] Assignee: The Research Foundation of State University of New York, Amherst, N.Y.

[21] Appl. No.: 529,224

[22] Filed: Sep. 15, 1995

[51] Int. Cl.⁶ .................................................. A61B 17/22
[52] U.S. Cl. ................................... 601/2; 128/660.03
[58] Field of Search ........................ 128/660.03; 601/2; 607/97; 606/159, 128; 604/20, 22

[56] References Cited

U.S. PATENT DOCUMENTS 4,227,407  10/1980  Drost.

OTHER PUBLICATIONS

Ernst et al., "Ability of high–intensity ultrasound to ablate human atherosclerotic plaques and minimize debris size," *Am. J. Cardiol.* 68:242–246 (1991).

Francis et al., "Enhancement of fibrinolysis in vitro by ultrasound," *J. Clin. Invest.* 90:2063–2068 (1992).

Blinc et al., "Characterization of ultrasound–potentiated fibrinolysis in vitro," *Blood* 81:2636–2643 (1993).

Harpaz et al., "Ultrasound accelerates urokinase–induced thrombosis and reperfusion," *American Heart Journal* 127:1211–1219 (1994).

*Primary Examiner*—Marvin M. Lateef
*Assistant Examiner*—Eleni Mantis Mercader
*Attorney, Agent, or Firm*—Nixon, Hargrave, Devans & Doyle

[57] ABSTRACT

The present invention is directed to inhibition of blood clot formation in a first segment of a blood vessel. Inhibition is effected in the first segment by exposing a second segment of the blood vessel to ultrasound. The second segment either contains the upstream region of the first segment or is upstream from this upstream region. A method for preventing a clot-induced event in a patient is also provided.

30 Claims, 3 Drawing Sheets

METHOD FOR INHIBITING CLOT FORMATION

FIELD OF THE INVENTION

The present invention relates generally to blood clotting, and more particularly to a method for inhibiting the formation of blood clots in blood vessels.

BACKGROUND OF THE INVENTION

Clotting of blood is an essential part of the hemostatic response and depends on a very delicate balance between a number of interrelated factors. Blood clotting consists of a series of biochemical reactions, commonly referred to as the clotting cascade. Each product of these reactions is an enzyme which catalyzes the next reaction in the sequence.

The clotting cascade is triggered by the activation of Hageman factor, also known as clotting factor XII. Activation of factor XII occurs when it comes into contact with negatively charged surfaces such as those that appear on exposed collagen fibers and on reacting platelet membranes. These conditions occur when blood vessels are punctured or attacked. Active Hageman factor (XIIa) then converts inactive plasma thromboplastin antecedent ("PTA") (factor XI) into its active form (XIa). XIa then convents plasma thromboplastin component ("PTC") (IX) to active plasma thromboplastin component (IXa), which, in turn converts Stuart-Prower factor (X) to its active form (Xa). Active Stuart-Prower factor converts the inactive form of prothrombin to the active enzyme, thrombin, which rapidly catalyzes the conversion of fibrinogen to fibrin which polymerizes to form a network of insoluble threads at the site of the injury.

Clotting (thrombosis) is the ultimate mechanism responsible for most blood vessel blockage, which in turn results in interrupted blood flow to the organ that the blood vessel perfuses. Strokes, heart attacks, and gangrene result from clotting on the arterial side of the circulation. Clotting on the venous side of the circulation is called phlebothrombosis and is also responsible for a number of substantial problems, such as thrombophlebitis, venous insufficiency, venous ulceration, and pulmonary embolism. (The latter can occur when a clot in an extremity dislodges and travels to the lung).

Clotting is also a major concern in surgical procedures which involve the grafting of blood vessels. Such clotting often occurs in the immediate post-operative period, within the first several hours after successful surgery has apparently been accomplished. During this time the endothelium (the inner most layer of blood vessel and the layer which is in contact with the blood), which has been disrupted or damaged by the surgical procedure, releases a variety of compounds, including cytokines, and activated white blood cells to cause tissue factor expression that stimulates clotting. Two common surgical procedures which can result in endothelium damage are coronary artery (major blood vessels feeding the heart musculature) bypass grafting surgery and creation of arteriovenous fistulas either by direct artery to vein anastomosis or by insertion of a graft of man made material (such as GORETEX™, a highly microporous poly tetrafluoroethylene, available from W.L. Gore and Associates, Inc., Newark, Del.) between an artery and a vein. More than 300,000 heart bypass procedures are performed in the United States each year to re-establish circulation to the heart. Creation of either an arteriovenous fistula or graft is an essential part of the preparation needed for the approximately 150,000 patients who are receiving regular hemodialysis to treat their end stage kidney disease. Endothelium damage and, consequently, the danger of post-procedure clotting, can also result from non-surgical procedures, such as angioplasty. Each year, more than 300,000 angioplasty procedures are performed to dilate narrowed segments of the coronary arteries. Unfortunately, because of the endothelial damage that can result from these procedures, recurrence of the narrowing (restenosis) or complete occlusion of the blood vessel can occur. Indeed the rate of restenosis of the coronary blood vessel following this balloon angioplasty is 40% within the first six months following the procedure. There are also an ever increasing number of angioplasty procedures being employed to dilate arteries that perfuse peripheral vascular beds, such as those of the legs, and restenosis remains a problem with these vessels as well.

To prevent the occurrence or reoccurrence of clotting, patients are frequently given anticoagulants after operations undertaken to repair blood vessels. Anticoagulants are also commonly used post-surgery to prevent venous clotting in patients with decreased motion. They are also used to prevent stroke and heart attack in patients who are proven to have, or suspected of having, abnormal blood vessels.

A variety of agents are presently used to control clotting. Urokinase, streptokinase, and (recombinant) tissue plasminogen activator ("rt-PA") are chemicals that cause clots to dissolve. These clot dissolving agents are generally used in emergency situations, such as a heart attack, where they lyse clots which have formed in the coronary arteries. Typically, these agents are injected into the blood stream or organ close to where the clot is suspected of having been formed. Although they will interrupt clotting anywhere that they reach an effective concentration in the blood stream, these agents are not used as prophylaxis against additional clotting because they have a high side-effect profile and, secondarily, because they are moderately (Streptokinase) or very (rt-PA) expensive. A recent study which evaluated the combined effects of angioplasty and thrombolytics in the treatment of arterial occlusive disease of peripheral vessels revealed a greater than 40% rate of bleeding (hemorrhagic) complications. Both urokinase and rt-PA also must be given intravenously posing another limitation on treatment. Further, patients may develop antibodies to these compounds which can restrict their repeated use.

Heparin and coumadin are two chemicals commonly used for prophylaxis to prevent clot formation. Heparin consists of sulfated simple chain polysaccharides of variable length and inhibits clotting by combining with antithrombin III, forming a complex capable of directly inhibiting the generation of thrombin as well as accelerating thrombin's decay. It is usually administered intravenously in a hospital setting. Even when administered subcutaneously, heparin is seldom used outside the hospital setting because changes in dose are frequently necessary (although low molecular weight heparin may be useful when administered subcutaneously to outpatients). Coumadin inhibits certain liver-made factors which are critical to the clotting process. Coumadin is relatively inexpensive, and is often prescribed as part of a long-term treatment regimen, lasting months or years. It is specifically used for prevention of recurrent heart attacks, strokes, thrombosis of artificial heart valves, and in a variety of other clinical circumstances.

Both heparin and coumadin act systemically rather than locally. Because of the systemic nature of treatment using these anticoagulants, careful monitoring of their levels in the blood is required. Anticoagulant levels within the therapeutic range, that is, between excessive anticoagulant (in which case the patient may experience undesirable bleeding elsewhere, such as from a cut, a bruise, or an ulcer) and insufficient anticoagulant, are often difficult to establish and maintain. Furthermore, even when blood levels are within the therapeutic range, there is a substantial increase in the incidence of bleeding. Patients who have an ulcer or other bleeding disorder are especially difficult to treat with these systemic anticoagulants.

Recently, aspirin has found wide use as a clot inhibitor, particularly with respect to clots on the arterial side of circulation. Aspirin inhibits the aggregation of platelets, which is often the first stage in clot development. Aspirin's effect is, therefore, also systemic and, consequently, use of this compound suffers some of the drawbacks associated with coumadin and heparin. In addition, aspirin's effect on platelets is long term, lasting a generation of platelets or about 7–10 days. Consequently, the ability of a patient's blood to coagulate, once impaired by aspirin, cannot be re-established without delay by simply discontinuing use of the aspirin.

It is apparent from the above discussion that a need exists for better ways to prevent clotting.

Ultrasonography is a noninvasive procedure utilizing reflection of high frequency sound waves from organs of the body to derive images. The imaging results from the variable reflection or absorption of wave energy by the different materials from which tissues and organs are comprised. The safety of the procedure is reflected by its extensive use as a tool to monitor the development of the fetus during gestation.

Ultrasound has also been used clinically to measure the flow of blood through blood vessels, as described in U.S. Pat. No. 4,227,407 to Drost. The device described therein measures the flow of fluid through a conduit by comparing the time of travel of ultrasound from an upstream ultrasound source to a downstream ultrasound detector with the time of travel from a downstream ultrasound source to an upstream ultrasound detector. The device and method are applicable generally to any fluid in any conduit and, specifically, to the measurement of blood flow through a blood vessel.

Ultrasound has also found clinical application in mechanically disrupting masses, such as gall stones and kidney stones, as well as in diathermy. Ultrasound is also being explored in the treatment of thrombotic vascular disease using two approaches: non-enzymatic and enzymatic (Siegel et al., "Clinical demonstration that catheter-delivered ultrasound energy reverses arterial vasoconstriction," *J. Am. Coll. Cardiol.* 20:732–735 (1992) and Francis et al., "Enhancement of fibrinolysis in vitro by ultrasound," *J. Clin. Invest.* 90:2063–2068 (1992)). Non-enzymatic treatment utilizes low-frequency (20–25 kHz), high-power (ca. 20 W) ultrasound to mechanically disrupt clots and atherosclerotic plaque, the debris from which is trapped distally (Ernst et al., "Ability of high-intensity ultrasound to ablate human atherosclerotic plaques and minimize debris size," *Am. J. Cardiol.* 68:242–246 (1991)). Complications arising from the intensity of the ultrasound used include heating of the blood, perforation of the vessel wall, and vessel wall damage (Ernst et al., "Ability of high-intensity ultrasound to ablate human atherosclerotic plaques and minimize debris size," *Am. J. Cardiol.* 68:242–246 (1991) and Gillebert et al., "Intracavitary ultrasound impairs left ventricular performance: presumed role of endocardial endothelium," *Am. J. Physiol.* 263:H857–H865 (1992)). Low-intensity, high-frequency ultrasound has been found to accelerate fibrinolysis catalyzed by enzymatic clot dissolving agents, such as rt-PA and Urokinase. By using such agents in combination with ultrasound, the intensity of the ultrasound necessary to dissolve clots is reduced to 1–3 W/cm$^2$, thereby avoiding the damaging effects of non-enzymatic ultrasound treatment.

Thus, the currently published information regarding the possible application of ultrasound to treat clotting disorders suggests that this modality is useful only for dissolution of established blood clots. Further, the energy levels of the sound waves that are effective to dissolve established clots can damage the blood vessel walls where the clots have formed or lodged. Treatment with lower levels of ultrasound energy is possible, but only when used to supplement chemical anticoagulants which may have systemic effects.

For the foregoing reasons, there remains a need for a method for preventing in vivo clot formation without the deleterious side effects or systemic impact of the chemicals presently used. Specifically, there remains a need for a method of preventing clot formation in a selected segment of a blood vessel.

SUMMARY OF THE INVENTION

The present invention relates to a method for inhibiting blood clot formation in a first segment of a blood vessel where inhibition of blood clot formation is desired. The first segment has an upstream region. According to the method of the subject invention, a second segment of the blood vessel is exposed to ultrasound thereby inhibiting blood clot formation in the first segment of the blood vessel. The second segment either contains the upstream region of the first segment or is upstream from this upstream region.

The invention further provides a method for preventing the occurrence of a clot-induced event in a patient. According to this method of the subject invention, a first segment of a blood vessel is suspected of having an abnormality which may promote blood clot formation is selected. The first segment also has an upstream region. A second segment of the blood vessel which either contains the upstream region of the first segment or lies upstream from this region is then exposed to ultrasound. This exposure of the second segment to ultrasound inhibits blood clot formation in the first segment, thereby preventing the occurrence of a clot-induced event in the patient.

According to the methods of the present invention, clot formation can be inhibited in specific, localized regions of the body, such as a blood vessel, including blood vessels of organs like the kidney, heart, and brain, without inhibiting clot formation elsewhere in the circulatory system. More particularly, the methods of this invention permit inhibition of clot formation in blood vessel segments with abnormalities which would tend to promote clot formation, and thus the method can be used as a prophylactic treatment, such as, for example, after a critical narrowing of a blood vessel is identified and prior to surgical repair of the vessel. The method of the invention also permits clot inhibition in vessels recently damaged or disrupted by surgical or other procedures, such as, for example, blood vessel grafts or angioplasty, or in vessels soon to be subjected to such damage or disruption.

The method of the invention offers several advantages over prior techniques used for inhibiting clot formation, including a localized effect and simplicity in use. Anticoagulants presently in use act systemically and reduce clotting throughout the patient's body. This necessitates constant monitoring and careful adjusting of anticoagulant blood levels to prevent undesirable bleeding elsewhere. The systemic effects of anticoagulant chemicals also make them nearly impossible to use in patients with ulcers or other bleeding disorders, even with monitoring. In contrast, the method of the invention inhibits clot formation in specific, localized regions of the body without preventing clotting elsewhere in the circulatory system. It is also less complicated because it does not require constant monitoring and adjustment of anticoagulant levels. Furthermore, the localized effect of the method permits its use in patients suffering from bleeding disorders without the potential danger of causing bleeding elsewhere. In addition, the method of the present invention could exhibit an advantageous property herein referred to as compensation. Blood tends to clot when it is moving slowly. When exposed to ultrasound in accordance with the methods of the present invention, blood that is moving slowly remains in the accoustical field longer and, consequently, receives a greater effective accoustical dose.

Although the mechanism of action is unknown, it is well known that clotting factors are continuously being formed in the blood stream and that these factors are carried downstream. Therefore, it is believed that interfering with these clotting factors upstream has anti-clotting effect downstream.

BRIEF DESCRIPTION OF THE DRAWINGS

These and other features and advantages of this invention will be evident from the following detailed description of preferred embodiments when read in conjunction with the accompanying drawings in which:

FIGS. 1a–1d show several first segments (shaded) and second segments (hatched) of a blood vessel spatially arranged in accordance with the present invention. In FIG. 1a, the second segment has a downstream end which lies within the first segment and an upstream end which lies upstream from the upstream region of the first segment. In FIG. 1b, the first segment lies entirely within the boundaries of the second segment. FIG. 1c depicts a spatial arrangement wherein the first and second segments are coterminous. In FIG. 1d, the entire second segment lies upstream from the upstream region of the first segment. The direction of blood flow is indicated by the arrow;

DETAILED DESCRIPTION

The present invention is directed to a method for inhibiting blood clot formation in a first segment of a blood vessel. The method comprises selecting a first segment of a blood vessel in which inhibition of blood clot formation is desired, and exposing a second segment of the blood vessel to ultrasound. The first segment has an upstream region, and the second segment is selected from the group of segments consisting of: a segment of the blood vessel containing the upstream region and a segment of the blood vessel located upstream from the upstream region. This exposure of the second segment to ultrasound inhibits blood clot formation in the first segment.

A blood vessel segment is defined as a collection of an infinite number of cross sectional slices. The upstream region of the first segment of the blood vessel is defined as that cross sectional slice which is upstream from all other cross sectional slices within the first segment. As used herein, a first cross sectional slice is upstream from a second cross sectional slice if blood, flowing in its natural course, passes through the first cross sectional slice before it passes through the second.

The first segment is selected on the basis of desirability of inhibition of blood clot formation therein. Inhibition of clot formation in a blood vessel segment may be desirable, for example, because of the existence of a condition therein which promotes clot formation. For example, the segment may experience reduced blood flow therethrough, caused by, for example, an abnormal reduction in cross section. Such narrowings in blood vessels commonly result from a build-up of arterial plaque (a condition often referred to as arteriosclerosis) or from a loss of blood vessel elasticity. Alternatively, reduction in blood flow can be caused by a congenital defect, such as coarctation of the aorta and other diseases, such as fibromuscular dysplasia. Vessels having reduced blood flow can be identified and localized by a number of well known techniques, such as, for example, Nuclear Magnetic Resonance Angiography, Radio Contrast Angiography, and Duplex Doppler Ultrasound. Because reduced blood flow in a segment of a blood vessel increases the risk of clot formation in such a segment, inhibition of blood clot formation in such a segment is frequently desirable.

Inhibition of clot formation in a blood vessel segment can also be desirable when the endothelium of the segment has been damaged or disrupted. The damaged or disrupted endothelium is believed to release increased amounts of compounds which stimulate clotting (such as von Willebrand factor, Tissue factor, and Plasminogen activator inhibitor-1) and decreased amounts of compounds which inhibit clotting (such as thrombomodulin and tissue plasminogen activator). Endothelium damage is an unavoidable consequence of certain medical manipulations, such as angioplasty and blood vessel grafting procedures, the latter of which include coronary artery bypass, fistula construction, and solid organ transplantation. In such cases, the exact position of the disrupted endothelium is invariably known and the first segment is one which includes the disrupted region. Endothelial damage can also result without the direct manipulation of the blood vessel during the course of invasive procedures. For example, cytokines (compounds released by cells which transmit very specific messages to neighboring cells) released by endotoxins during sepsis or stimulated by excess local levels of oxidants can alter or disrupt this sensitive innermost layer of vascular wall and stimulate local or downstream clot formation.

Although observation of a clot-promoting condition in a segment, such as a congenital narrowing or arteriosclerotic plaque, is sufficient basis for inhibiting clot formation therein, it should be understood that it is not a necessary basis for employing the methods of the present invention. The desirability of inhibiting clot formation in a segment can be based, for example, on observation of actual clot formation or on observation of symptoms which indicate clot formation is beginning or imminent. Symptoms which indicate that clots are forming include skin discoloration, reduced skin temperature, pain, and swelling. The presence of certain chemicals in the blood which are implicated in the clotting process, such as fibrinogen breakdown products, D-Dimer, and fibrinopeptide A (which are usually detected in the peripheral blood only in very severe cases), can also be used as indicators of clot formation.

For example, the methods of the present invention can inhibit blood clot formation in a first segment of an arterial blood vessel and the smaller downstream vessels into which it divides in the organ (such as a lung, a kidney, a liver, or a spleen) or tissue (such as a leg, a foot, an arm, or a hand) which it perfuses. In many cases, identification of the exact vessel in which blood clots are forming is impossible. This is frequently the case when blood clots form in the minor blood vessels. In such cases it is preferable to select each of the suspected blood vessels as a first segment. Often this becomes equivalent to selecting each blood vessel in an entire region, such as a foot or a leg, as a segment in which clot inhibition is desired. Accordingly, it should be understood that the desirability of clot inhibition in a particular segment can be made without precisely defining the segment as long as the treatment is applied upstream from the upstream region.

The first segment is preferably of sufficient length to ensure inclusion of the entire portion of a blood vessel in which inhibition of clot formation is desired. Accordingly, it may be desirable to define the first segment, for example, to include the entire region of suspected clot formation or reduced blood flow.

Figure 1A:
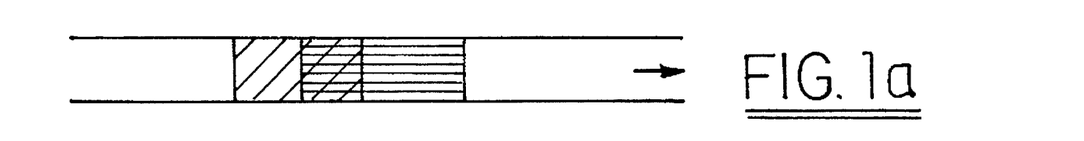
Figure 1B:
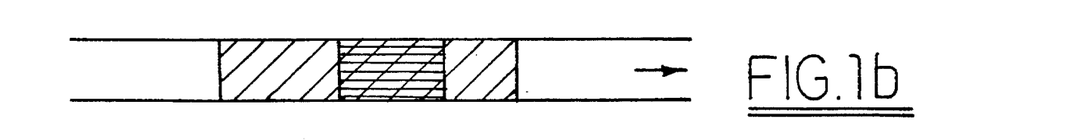
Figure 1C:
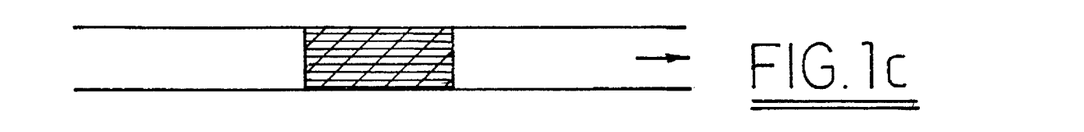
Figure 1D:
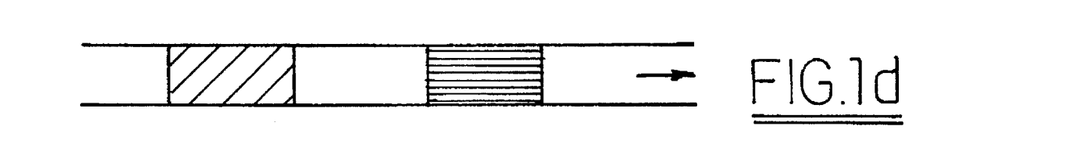

Blood clot formation in the first segment is inhibited by exposing a second segment of the blood vessel to ultrasound. The second segment can be any segment of the blood vessel which contains the upstream region of the first segment. The second segment can, for example, have a downstream end which lies within the first segment and an upstream end which lies upstream from the upstream region of the first segment, as shown in FIG. 1a. The second segment can also be such that the first segment lies entirely within the second segment, for example, as shown in FIG. 1b. The second segment can also be coterminous with the first segment, as shown in FIG. 1c. Alternatively, the second segment can be any segment of blood vessel which lies upstream from the upstream region of the first segment as shown in FIG. 1d. As used in the context of comparing the spatial relationship of a second segment of a blood vessel with the upstream region of a first segment of the blood vessel, the second segment lies upstream from the upstream region if, and only if, blood, in its normal course of flow, leaves the second segment prior to crossing the upstream region of the first segment.

The second segment, so long as it spatially relates to the first segment as detailed above, may be of any desirable length. The preferred length and location of the second segment is determined in view of the desirability or undesirability of clot inhibition in various regions of the blood vessel, recognizing, of course, that clot formation is inhibited within and downstream from the second segment. For example, referring to FIG. 2, if clot inhibition is desired in segment X, appropriate second segments would include those labeled W or Z. However, exposing the segment labeled W will result in clot inhibition in segment Y as well as in segment X. As the skilled art-worker will note, this may be desirable, such as, for example, where both segments X and Y are critically narrowed or reduced, or it may be undesirable, for example, where Y contains a defect that renders it prone to bleeding. Generally, to exploit the non-systemic nature of ultrasound treatment, it is preferable to direct clot inhibition only at the specific region where clot inhibition is required thus permitting normal clotting activity elsewhere. Consequently, it is preferred that exposure be delivered between the first segment and the heart, if the first segment is arterial, and between the first segment and the organ or tissue bed it drains, if the first segment is venous. Where the first segment is arterial, the second segment is preferably selected so that at least a portion of the second segment lies within the organ blood vessel which supplies the downstream blood vessel containing the first segment. Furthermore, it may be desirable that the second segment lie as close to the first segment as practicable or even that the second segment be coterminous with the first segment. Of course, in the case of organ protection, the terminal blood vessels in the organ are too small and too numerous to precisely direct the ultrasound treatment to individual terminal blood vessels. In such cases, exposure of the blood vessel perfusing the organ immediately upstream from the organ is preferred.

Figure 2:
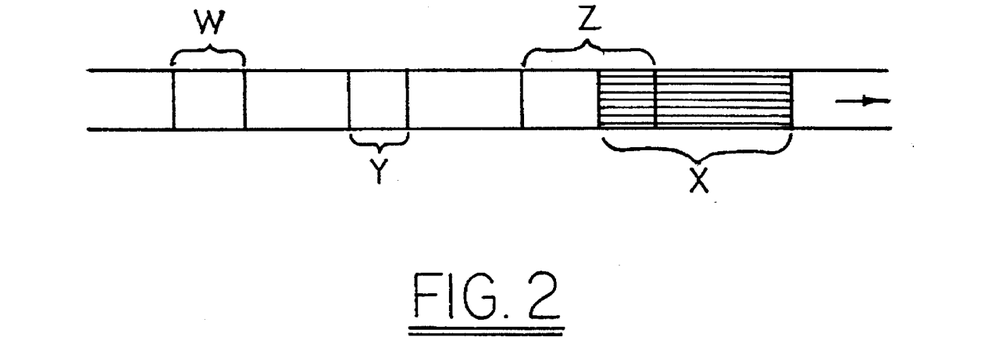
FIG. 2 depicts a blood vessel having a first segment, labeled X, and two alternative second segments, labeled W and Z. Another segment, Y, is shown in which clot formation is inhibited by choosing segment W as the second segment and in which clot formation is not inhibited by choosing segment Z as the second segment. The direction of blood flow is indicated by the arrow.
Figure 3A:
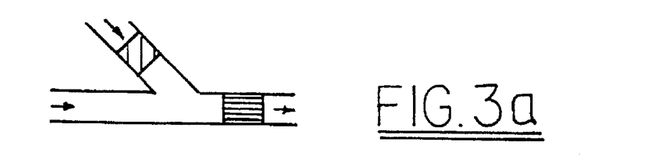
FIGS. 3a–3i represent a first segment (shaded) and a second segment (hatched) which are spatially arranged such that the two segments are segments of a (single) blood vessel, as defined herein for purposes of this invention, and such that exposure of the second segment to ultrasound inhibits clot formation in the first segment.
Figure 3B:
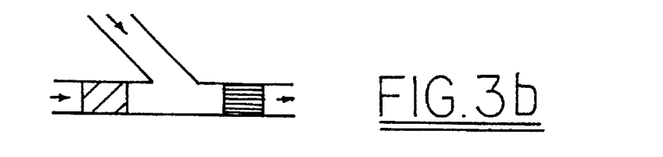
Figure 3C:
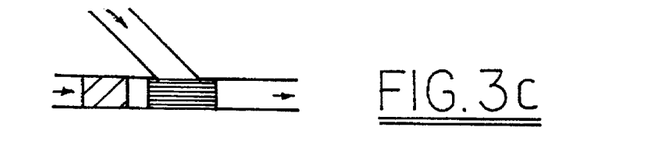
Figure 3D:
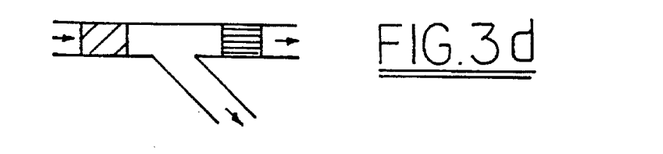
Figure 3E:
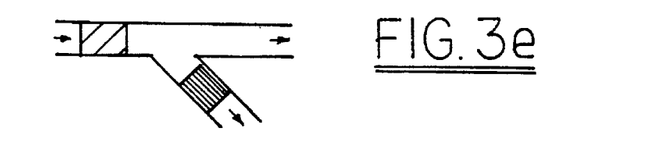
Figure 3F:
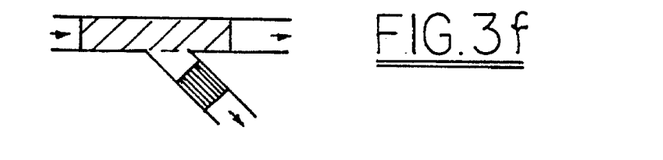
Figure 3G:
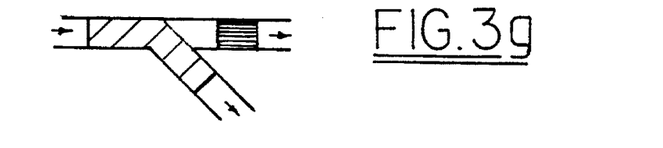
Figure 3H:
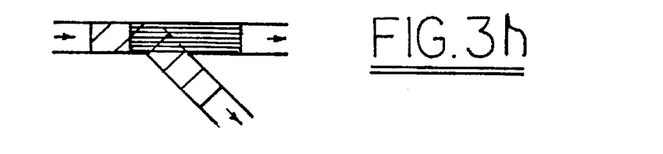
Figure 3I:
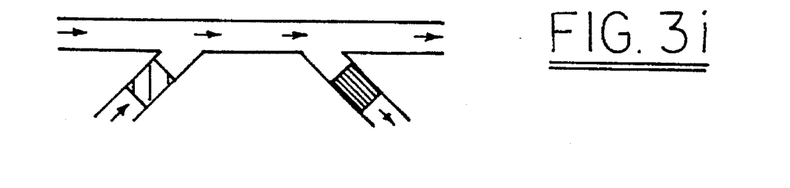
Figure 3J:
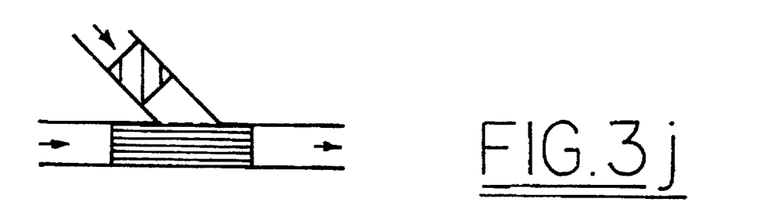
In FIGS. 3j–3n, the spatial relationship of the first segment (shaded) and second segment (hatched) fails to effect clot inhibition in the first segment. Arrows indicate direction of blood flow.
Figure 3K:
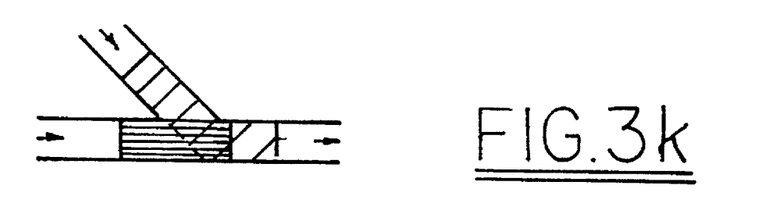
Figure 3L:
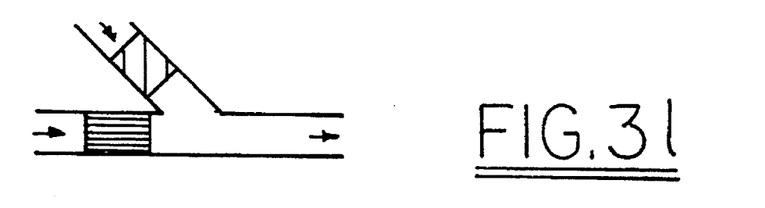
Figure 3M:
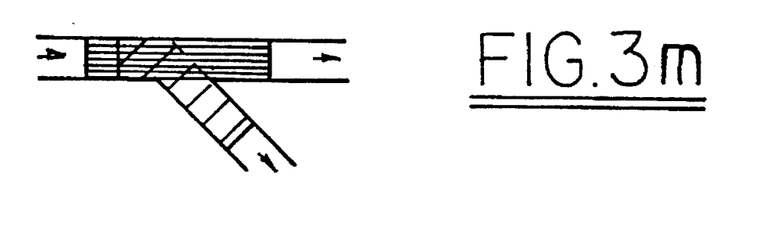
Figure 3N:
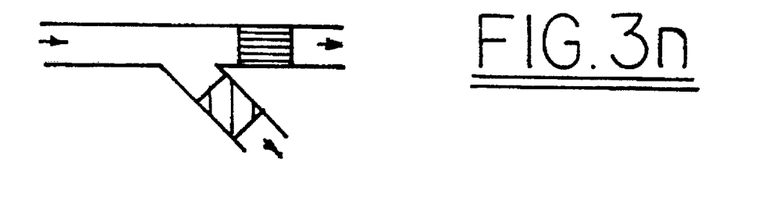

An additional factor which should be considered in determining the length and location of the second segment is that the clot inhibiting effects of an ultrasound exposure may decrease with time. In a flowing medium, such as blood, this implies that clot inhibiting effects decrease with distance along the blood vessel between the exposed second segment and the first segment. Referring to FIG. 2, the affect of exposure on blood clot formation in the first segment X depends on a variety of factors, including, primarily, distance and flow rate. Therefore, all else being equal, exposure at Z will presumably have a greater clot inhibiting effect at X than will exposure at W.

In addition, it is advantageous to choose a second segment so that no side branches exist between the first and second segments, that is, so that all flow through the second segment continues through the first segment. When configured in this manner, if clotting starts to occur in the first segment, the blood flow through the second segment will decrease and the effective localized dose of ultrasound applied to the blood will increase. If clotting is reversed the rate of blood flow through the second segment will increase and the effective dose will down regulate in compensation.

As used herein, two segments are both considered to be of a (single) blood vessel if both segments are on the same side of the circulatory system (that is, both segments are arterial or both segments are venous) and if at least some portion of the blood passing through either segment also passes through the upstream region of the other segment in the course of its natural flow. Accordingly, the present invention provides methods for preventing blood clot formation in a first segment by exposing a second segment, where the first and second segments are spatially related as depicted in FIGS. 3a–3i. Where the first and second segments are spatially related as depicted in FIGS. 3j–3n, blood clot inhibition is not effected in the first segment.

The ultrasound to which the blood vessel is exposed can have a frequency of between 500 kHz and 40 MHz, more preferably between 1 and 7.5 MHz, most preferably between 1.5 and 4 MHz.

The average intensity of the ultrasound at the exterior surface of the blood vessel can be between about 1 and 100 $mW/cm^2$, more preferably between about 7 and 50 $mW/cm^2$.

The ultrasound can be continuous or non-continuous. When the ultrasound is non-continuous, the intensity of ultrasound varies with time, such as, for example, a periodic on/off step-function where the duty cycle is defined as ((time on)/(time off+time on)) per cycle. In such a non-continuous exposure, the duty cycle can be between 3% and 100% while still providing anti-clotting effects. For example, blood clot formation can be inhibited in accordance with the present invention by exposing the second segment to ultrasound for 1 minute every 10 minutes. It is understood that this invention is not limited to the two intensity vs. time profiles discussed herein (i.e. non-continuous step and continuous and constant) and that other intensity vs. time functions such as, for example, sinusoidal, sawtooth, ramp, triangular and combinations thereof, are within the scope of this invention, whether they be periodic, a-periodic or quasi-periodic.

The ultrasound to which the segment is exposed can be produced by any suitable source. Suitable sources include therapeutic ultrasound instruments (such as, for example, the Intertect 225P, Chattanooga Corp., Chattanooga, Tenn.) and piezoelectric crystals. Selection of a suitable source for a particular application is not critical when the source is to be mounted outside the body. However, when use of the source in vivo is contemplated, size, material of fabrication, and heating characteristics of the source must be considered in the selection. Suitable ultrasound sources include LTZ-2 piezoelectric ceramics, available from Transducer Products, Torrington, Conn., operated in a thickness mode and LUCITE™ (poly(methyl methacrylate)) backed, with no impedance matching and with a nominal resonance frequency of 2 MHz. Ultrasound sources with such an LTZ-2 piezoelectric crystal include the Transonic 1R, 2S, 2RB, 3R, and 3S Flowprobes, available from Transonic Systems, Inc., Ithaca, N.Y. and described in U.S. Pat. No. 4,227,407 to Drost, the disclosure of which is hereby incorporated by reference.

The power output of the ultrasound source is selected based on the distance from the source to the second segment and the nature of the intervening medium. Where the ultrasound source is placed directly on or in close proximity to the surface of the second segment, the power can be between 0.2 and 2.0 mW, preferably between 0.6 and 1.0 mW. The maximum peak power of the ultrasound source can be between 0.1 and 5.0 W/cm$^2$, preferably between 0.3 and 2.0 W/cm$^2$.

In one embodiment of the invention, the ultrasound source is mounted external to the patient and ultrasound is directed to the second segment through the patient's skin. This method is non-invasive and especially advantageous where the second segment lies close to the surface of the skin. For vessels located farther below the skin's surface, simply mounting the ultrasound source on the skin frequently exposes unselected vessels and, consequently, reduces the extent to which clot inhibition is localized. Accordingly, for vessels located farther below the skin's surface, it is preferred that the ultrasound be directed specifically at the second segment. For example, an ultrasound source external to the body may be focused on the second segment using ultrasound focusing methods well known in the art, such as, for example, those described in Hokarson, et al., "Ultrasound arteriography: A new approach to arterial visualization," *Biomed. Eng.* 6:420 (1971), which is hereby incorporated by reference.

Alternatively, ultrasound can be guided to specific locations in the body by employing the devices and procedures commonly used to mechanically disrupt masses within the body. For example, a catheter containing a device capable of emitting the desired ultrasound can be inserted into the body through a small incision made in a femoral or brachial artery and threaded inside the blood vessel to the second segment.

As a third alternative, ultrasound can be directed to a second segment by mounting the ultrasound source directly on, or in close proximity to, the exterior surface of the second segment. This method is advantageous because it permits precise exposure of the second segment, and minimizes exposure elsewhere. Furthermore, because the amount of intervening material is minimized, the power required is substantially lower than when the ultrasound source is external to the body. However, because this method requires access to the blood vessel, it is especially preferred as a complement to an invasive surgical procedure, such as, for example, blood vessel grafting procedures. Preferably, the second segment is exposed during the surgical procedure. The ultrasound source can be removed prior to completion of the procedure, or, alternatively, ultrasound exposure can be continued for a period of time, such as 4 hours, immediately following the procedure. The method, thus employed, can prevent a clot formation during the operation and post-operative period, such as to prevent post-operative thrombosis.

The present invention further relates to a method of preventing a clot-induced event in a patient. As used herein, "clot-induced event" means any condition or complication which is caused or exacerbated by the formation of clots in the circulatory system, such as, for example, heart attack, stroke, and arterial thrombosis. The method includes selecting a first segment of a blood vessel having an upstream region and suspected of having an abnormality which may promote clot formation. A second segment of the blood vessel is then exposed to ultrasound. The second segment is either a segment of the blood vessel containing the upstream region or a segment of the blood vessel located upstream from the upstream region. Exposure of the second segment inhibits blood clot formation in the first segment, thereby preventing the clot induced event in the patient.

The abnormality can be any condition of the blood vessel which restricts blood flow therethrough. For example, there may exist a reduction in the cross section of the blood vessel caused by, for example, a build up of arterial plaque, often referred to as arteriosclerosis, as well as a loss of blood vessel elasticity. Alternatively, reduction in blood flow may be caused by a congenital defect. These conditions can be diagnosed and vessels having reduced blood flow can be identified and localized by a number of well known techniques, such as, for example Nuclear Magnetic Resonance Angiography, Radio Contrast Angiography, and Duplex Doppler Ultrasound. The abnormality may also be suggested by observation of blood clot production, or the effects thereof, or by elevated levels of certain chemicals which are implicated in the clotting process, such as fibrinogen breakdown products, D-Dimer, and fibrinopeptide A (which are usually detected in the peripheral blood only in very severe cases).

The following examples will serve to further illustrate the invention.

EXAMPLES

Example 1

Materials and Methods

All experiments were performed using White New Zealand female rabbits. Using aseptic technique and Sodium Pentobarbital anesthesia with local Lidocaine HCl anesthesia at the sites of incision, a silastic catheter was placed in the right jugular vein and advanced 2–3 cm. The catheter was flushed and filled with very dilute heparin (25 U/ml)(Elkins-Sinn Inc., Cherry Hill, N.J.). Using a retroperitoneal approach, a 2RB ultrasonic flowprobe (described in U.S.

Pat. No. 4,227,407 to Drost and available from Transonic Systems Inc., Ithaca, N.Y.) was implanted perivascularly on the left renal artery in a suprarenal position. The ultrasonic flowprobe contains a 3.6 MHz piezoelectric ultrasound source having a probe power of 0.8 mW, a maximum peak power of 0.7 W/cm$^2$ and an average intensity of 14 mW/cm$^2$. The probe was then coated with either sterile surgical jelly in the case of acute experiments or with 1–2 ml. of rabbit blood for survival surgeries. After ascertaining that the probe was functioning, the incision was closed with sutures, and in the case of survival surgery, the probe and catheter were tunnelled subcutaneously to emerge below the point of the scapula and then placed in the pocket of a fitted red jacket.

Acute experiments were performed immediately upon completion of surgery and under anesthesia. The rabbit received an injection of 150 mg/kg aminocaproic acid (Abbott Labs, Chicago, Ill.) via the jugular vein catheter. Fifteen minutes later, a dose of 3 ml/kg Thromboplastin (Sigma Co., St. Louis, Mo.) was infused over a ten minute period. The animal was monitored for respiration, level of anesthesia, and depending on the experiment, renal blood flow, for 60 minutes. At this point the animal was euthanized with an overdose of pentobarbital, and the lung, liver, spleen, and both kidneys were immediately frozen for indirect immunofluorescence microscopy examination ("IF"). In some experiments, Thrombin (Sigma Co., St. Louis, Mo.) totalling 300, 500, or 700 NIHU/kg was infused over the 60 minute period instead of Thromboplastin. In control experiments, the renal flow probe was implanted and ascertained to be working, but was not turned on during the experiment.

In experiments involving a Lipopolysaccharide ("LPS") component of *E. coli* endotoxin (Difco Laboratories, Detroit, Mich.), the rabbits were allowed to recover from surgery and utilized the following day. Three groups of rabbits were studied in each set of experiments. In one set of experiments, two bolus doses of LPS, 100 µg/kg each, spaced 24 hours apart, were administered to each of the rabbits, and the rabbits were euthanized 4 hours after the second dose. Renal blood flow ("RBF") was monitored during the four hours immediately following LPS administration each day. For controls, the probe was turned off. In some experiments the probe was on intermittently. In a second set of experiments, rabbits received pretreatment for 4 days with 12.5 mg/kg/day Cortisone (Sigma Co., St. Louis) intramuscularly ("IM"), followed by one dose of 100 µg/kg LPS. Again, the probe was on, off, or on intermittently. As in the first set of experiments, tissue samples were obtained for IF studies.

Immunofluorescence microscopy was used to examine organs for the presence of fibrin as evidence of clot formation using the procedure described by Andres et al., *J. Clin. Invest.* 49:2106–2118 (1970), which is hereby incorporated by reference. All slides were blindly prepared and blindly evaluated semiquantitatively on a scale from 1 to 3 by a single individual.

Example 2

Effects of Ultrasound on Thromboplastin-Aminocaproic Acid Induced Clotting

Five rabbits, prepared as described above in Example 1, received 150 mg/kg of aminocaproic acid (to prevent endogenous fibrinolysis) via the jugular vein catheter. Fifteen minutes later, a dose of 3 ml/kg of Thromboplastin was infused over a 10 minute period. Two sets of experiments were performed. In one, the ultrasound source was left off, while in the other, it was turned on for the 1 hour period following thromboplastin infusion. After one hour the rabbits were all euthanized and the organs harvested. Table 1 presents the mean (± standard deviation) level of clotting observed in each of the harvested organs.

TABLE 1

| Ultrasound Source | Left Kidney | Right Kidney | Lung | Liver | Spleen |
|---|---|---|---|---|---|
| ON (n = 16) | 1.1 ± 0.7 | 1.7 ± 0.8* | 0.77 ± 0.5 | 1.5 ± 0.4 | 1.4 ± 0.5 |
| OFF (n = 12) | 2.0 ± 0.6** | 1.8 ± 0.6 | 0.84 ± 0.3 | 1.3 ± 0.3 | 1.6 ± 0.4 |

*P = 0.02, right vs. left kidney
**P = 0.001, probe on vs. probe off

Example 3

Effects of Ultrasound on Cortisonelipopolysaccharide Induced Clotting

Four rabbits, prepared as described in Example 1 and permitted to recover from surgery for 24 hours, were each given 12.5 mg/kg of Cortisone IM each day for four consecutive days. On the last day 100 µg/kg of LPS was administered, and, four hours after LPS injection, the rabbit was euthanized. Lung, liver, spleen, and both kidneys were taken for IF. The ultrasound source was on continuously from 30 minutes before to 4 hours after LPS injection. The results are shown in Table 2. Clotting was observed in the spleen and the lung but not in the left kidney. Control rabbits treated according to the above protocol but not fitted with an ultrasound source exhibited severe clotting in the left kidney.

TABLE 2

| Ultrasound Source | Left | Lung | Liver | Spleen |
|---|---|---|---|---|
| ON (n = 4) | 0.2 ± 0.4 | 0.8 ± 0.1 | 0 | 1.1 ± 0.3 |
| OFF (n = 6*) | 2.7 ± 0.7 | 0.8 ± 0.5 | 1.2 ± 0.5 | 2.3 ± 0.8 |

*historical control

Example 4

Effect of Intermittent Ultrasound on Cortisonelipopolysaccharide Induced Clotting Six rabbits were prepared and treated exactly as the rabbits from Example 3 except that the ultrasound source was on for one minute every ten minutes from 30 minutes before LPS injection to 1½ hour after injection. Thereafter, the ultrasound source was on for one minute every 30 minutes until the rabbit was euthanized. Table 3 presents the results along with the continuous exposure and no exposure results of the previous example. Clotting was observed in the lung, liver, and spleen and but not in the left kidney.

TABLE 3

| Ultrasound Source | Left Kidney | Lung | Liver | Spleen |
| --- | --- | --- | --- | --- |
| ON (n = 4) | 0.2 ± 0.4 | 0.8 ± 0.1 | 0 | 1.1 ± 0.3 |
| Intermittent (n = 6) | 0.7 ± 0.6 | 1.1 ± 0.3 | 1.1 ± 0.4 | 1.5 ± 0.6 |
| OFF (n = 6*) | 2.7 ± 0.7 | 0.8 ± 0.5 | 1.2 ± 0.5 | 2.3 ± 0.8 |

*historical controls

Example 5

Effect of Ultrasound on Lipopolysaccharide Induced Clotting

Rabbits, prepared in accordance with Example 1 and permitted to recover from surgery for 24 hours, were each given two 100 μg/kg bolus doses of LPS spaced 24 hours apart. The rabbits were euthanized 4 hours after the second dose. The rabbits were divided into 3 groups. In the first group the ultrasound source was not activated. The second and third groups were exposed to ultrasound during the four hours immediately after administering the second bolus. The second group was exposed to ultrasound continuously over the entire 4 hour period whereas the third group was exposed to ultrasound 1 minute every 10 minutes for the first 1½ hour following administration of second bolus and, then for one minute every 30 minutes until euthanization. Results are presented in Table 4.

TABLE 4

| Ultrasound Source | Left Kidney | Right Kidney | Lung | Liver | Spleen |
| --- | --- | --- | --- | --- | --- |
| ON (n = 6) | 0.5 ± 0.8 | 1.0 ± 1.3 | 1.1 ± 0.5 | 1.0 ± 0.9 | 1.6 ± 0.5 |
| Intermittent (n = 6) | 1.8 ± 0.6 | 3.0 ± 0.0 | 1.8 ± 0.3 | 2.5 ± 0.0 | 2.8 ± 0.3 |
| OFF (n = 6) | 2.0* ± 1.0 | 1.8 ± 1.0 | 1.8 ± 0.5 | 1.7 ± 1.0 | 1.8 ± 0.7 |

*P = 0.04, probe off vs. probe on.

Example 6

Investigation of the Effect of Ultrasound Exposure on Clotting Induced by Thrombin Rabbits prepared as described in Example 1 received a 150 mg/kg dose of aminocaproic acid to inhibit endogenous fibrinolysis via the jugular vein catheter. Fifteen minutes thereafter, a dose of Thrombin totaling 300, 500 or 700 NIHU/kg was infused over a 60 minute period. Comparison of right kidney to left kidney effects and probe on vs. probe off data are presented in Table 5. No significant differences were observed. These data suggest that ultrasound, as used in the methods of the present invention, does not interfere with the thrombin-mediated catalysis of fibrinogen to fibrin or with the polymerization of fibrin. Rather, ultrasound appears to affect the clotting cascade at some point earlier than the conversion of fibrinogen to fibrin.

TABLE 5

| Thrombin Dose | Ultrasound Source | Left Kidney | Right Kidney | Liver | Spleen |
| --- | --- | --- | --- | --- | --- |
| 300 NIHU | ON (n = 8) | 1.2 ± 0.7 | 1.3 ± 0.8 | 1.6 ± 0.9 | 1.0 ± 0.8 |
| | OFF (n = 8) | 1.6 ± 1.0 | 1.6 ± 1.0 | 1.4 ± 0.7 | 1.4 ± 1.2 |
| 500 NIHU | ON (n = 4) | 2.6 ± 0.2 | 2.6 ± 0.2 | 1.9 ± 0.2 | 2.0 ± 0.9 |
| | OFF (n = 4) | 2.8 ± 0.3 | 2.8 ± 0.3 | 2.5 ± 0.4 | 1.9 ± 0.9 |
| 700 NIHU | ON (n = 3) | 3.0 | 3.0 | a | a |
| | OFF (n = 3) | 3.0 | 3.0 | | | a. Liver and spleen not evaluated for clot formation.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method for inhibiting blood clot formation in a first segment of a blood vessel, said method comprising:
   selecting a first segment of a blood vessel in which inhibition of blood clot formation is desired, wherein the first segment has an upstream region; and
   exposing a second segment of the blood vessel to ultrasound, wherein the second segment is selected from the group of segments consisting of: a segment of the blood vessel containing the upstream region; and a segment of the blood vessel located upstream from the upstream region; wherein said exposure of the second segment to the ultrasound inhibits blood clot formation in the first segment of the blood vessel.

2. The method of claim 1, wherein the second segment is a segment of the blood vessel containing the upstream region.

3. The method of claim 1, wherein the second segment is a segment of the blood vessel located upstream from the upstream region.

4. The method of claim 1, wherein the first segment is located in an organ or a tissue.

5. The method of claim 4, wherein the organ is selected from the group consisting of a kidney, a lung, a liver, and a spleen.

6. The method of claim 4, wherein the tissue is selected from the group consisting of a foot, a leg, a hand, and an arm.

7. The method of claim 1, wherein the ultrasound has a frequency between about 1 and about 7.5 MHz.

8. The method of claim 1, wherein the second segment has an exterior surface and wherein the ultrasound has an average intensity between about 7 and about 50 mW/cm$^2$ at the exterior surface.

9. The method of claim 1, wherein said exposure is continuous.

10. The method of claim 1, wherein said exposure is non-continuous.

11. The method of claim 10, wherein said non-continuous exposure has an intensity-time profile of a square wave with a duty cycle of between about 3 and 100%.

12. The method of claim 1 wherein said exposing comprises providing an ultrasound source and directing the ultrasound from the ultrasound source to the second segment.

13. The method of claim 12, wherein the second segment is located inside a patient, the patient having a skin, wherein the ultrasound source is mounted externally to the patient, and wherein the ultrasound is directed to the second segment through the skin of the patient.

14. The method of claim 13, wherein the directed ultrasound is focused on the second segment.

15. The method of claim 13, wherein the skin has an external surface, and wherein the ultrasound source is mounted directly on the external surface of the skin and directly over the second segment.

16. The method of claim 12, wherein the second segment has an exterior surface, and wherein the ultrasound source is mounted directly on the exterior surface of the second segment.

17. The method of claim 16, wherein the ultrasound source has a probe power between about 0.6 and about 1.0 mW.

18. The method of claim 16, wherein the ultrasound source has a maximum peak power between about 0.3 and about 2.0 W/cm$^2$.

19. The method of claim 12, wherein the second segment has an exterior surface, and wherein the ultrasound source is mounted in close proximity to the exterior surface of the second segment.

20. The method of claim 12, wherein the ultrasound source is inserted into the blood vessel.

21. The method of claim 1, wherein endothelium of the first segment is damaged or disrupted.

22. The method of claim 21, wherein endothelium of the first segment is damaged or disrupted in the course of a medical procedure.

23. The method of claim 22, wherein the medical procedure comprises an angioplasty procedure.

24. The method of claim 22, wherein the medical procedure comprises a blood vessel grafting procedure.

25. The method of claim 24, wherein the second segment of the blood vessel has an exterior surface and wherein said exposing comprises mounting an ultrasound source directly on the exterior surface of the second segment.

26. The method of claim 25, wherein the second segment is exposed during the blood vessel grafting procedure, and the ultrasound source is removed prior to completion of the blood vessel grafting procedure.

27. The method of claim 22, wherein said exposing is performed during a period of time comprising 4 hours immediately following completion of the medical procedure.

28. A method of preventing a clot-induced event in a patient, said method comprising:

selecting a first segment of a blood vessel blood clot formation, the first segment having an upstream region; and exposing a second segment of the blood vessel to ultrasound, wherein the second segment is selected from the group of segments consisting of: a segment of the blood vessel containing the upstream region and a segment of the blood vessel located upstream from the upstream region; wherein said exposure of the second segment to the ultrasound inhibits blood clot formation in the first segment of the blood vessel, thereby preventing the clot-induced event in the patient.

29. The method of claim 28, wherein the clot-induced event is selected from the group consisting of a stroke and a heart attack.

30. The method of claim 28, wherein the abnormality is selected from the group consisting of arteriosclerosis and a congenital defect.

* * * * *